United States Patent [19]

Kobayashi

[11] Patent Number: 5,068,438

[45] Date of Patent: Nov. 26, 1991

[54] PROCESS FOR SURFACE TREATMENT OF N-ALKYL-N'PHENYL-P-PHENYLENEDIAMINE

[75] Inventor: Katsumi Kobayashi, Yokkaichi, Japan

[73] Assignee: Mitsubishi Monsanto Chemical Company, Tokyo, Japan

[21] Appl. No.: 449,103

[22] Filed: Dec. 7, 1989

Related U.S. Application Data

[63] Continuation of Ser. No. 244,649, Sep. 13, 1988, abandoned, which is a continuation of Ser. No. 796,627, Nov. 8, 1985, abandoned.

[51] Int. Cl.$^5$ .................. C07C 209/82; C07C 211/55
[52] U.S. Cl. .................................... 564/434; 71/64.03; 71/64.04; 71/64.05; 71/DIG. 1; 534/887
[58] Field of Search ............ 564/434; 71/64.03, 64.04, 71/64.05, DIG. 1; 534/887

[56] References Cited

U.S. PATENT DOCUMENTS

| 1,891,891 | 12/1932 | Luft et al. | 534/887 |
| 2,436,771 | 2/1948 | Hood | 260/704 |
| 4,554,004 | 11/1985 | Bierman et al. | 71/64.04 |

OTHER PUBLICATIONS

Sumitomo Chemical "Chemical Abstracts" No. 111,121n, vol. 97, (1982).

Primary Examiner—Richard L. Raymond
Attorney, Agent, or Firm—Burgess, Ryan & Wayne

[57] ABSTRACT

N-Alkyl-N'-phenyl-p-phenylenediamine particles, which are not easily broken during transportation or in a hopper and can be easily automatically metered, are prepared by a surface treating process wherein granulated N-alkyl-N'-phenyl-p-phenylenediamine particles are charged in a rotatable vessel and the vessel is then rotated at a temperature lower than the melting point of the N-alkyl-N'-phenyl-p-phenylenediamine, to cause the N-alkyl-N'-phenyl-p-phenylenediamine particles to freely flow.

10 Claims, No Drawings

PROCESS FOR SURFACE TREATMENT OF N-ALKYL-N'PHENYL-P-PHENYLENEDIAMINE

This application is a continuation, of application Ser. No. 244,649, filed 9-13-88, now abandoned, which in turn is a continuation of application Ser. No. 796,627, filed 11/8/85, now abandoned.

BACKGROUND OF THE INVENTION

1. Field of the Invention

The present invention relates to a process for the surface treatment of N-alkyl-N'-phenyl-p-phenylenediamine particles, in which the surface properties of N-alkyl-N'-phenyl-p-phenylenediamine particles are changed by causing the particles to freely flow in a vessel maintained at a temperature lower than the melting point of the diamine.

N-Alkyl-N'-phenyl-p-phenylenediamines, for example, N-isopropyl-N'-phenyl-p-phenylenediamine and N-(1,3-dimethylbutyl)-N'-phenyl-p-phenylenediamine, are used in large quantities as stabilizers such as antioxidants for rubbers or polymerization inhibitors for unsaturated carboxylic acids or esters thereof, and are marketed in the form of powders, flakes or granules.

2. Description of the Related Art

The above-mentioned marketed products of N-alkyl-N'-phenyl-p-phenylenediamines, especially flakes, are readily broken and powdered during transportation, and as in the case of powders, dust is scattered during use thereof and the working environment is deteriorated. Moreover, in the case of a compound having a low melting point, such as N-(1,3-dimethylbutyl)-N'-phenyl-p-phenylenediamine, formation of a small amount of powder causes agglomeration and a compaction phenomenon is induced. Therefore, fine powder contained in the product must be removed to avoid the occurrence of this phenomenon, and accordingly, a complicated sieving operation becomes necessary, drastically reducing the yield.

As the result of recent rationalization in the manufacture of rubber products such as tires, automatic metering is performed at the compounding step and this necessitates that rubber additives such as antioxidants be weighed continuously and in a given quantity. It is considered that granulation of the N-alkyl-N'-phenyl-p-phenylenediamines makes a great contribution to the above rationalization.

As means for granulating N-alkyl-N'-phenyl-p-phenylenediamines, there have been proposed, for example, a process in which a melt of an N-alkyl-N'-phenyl-p-phenylenediamine is incorporated or dropped into an aqueous solution of a hydrophilic polymeric compound or a surface active agent and the mixture is solidified, and a process in which the melt is dropped onto a steel belt to effect solidification. Furthermore, a process is known in which a powdery N-alkyl-N'-phenyl-p-phenylenediamine is dispersed in water containing an organic solvent and the dispersion is heated at a temperature lower than the boiling point of water to effect granulation.

In the conventional processes, granular products are obtained by rapidly cooling melts, and therefore, the particles are brittle and fine powders are generated by breakage during transportation or in a hopper; although the resistance to disintegration is improved as compared with flaky products. The pulverized fine powders are accumulated in the bottom portion of the hopper and have poor flowability. Accordingly, agglomeration or compaction occurs; making automatic metering difficult and clogging the discharge opening of the hopper. Especially, when the melt is dropped on the steel belt, the formed particles are obtained in the dry state, and fine powders formed by breakage during transportation in the preparation process adhere to the surfaces of other particles to reduce the flowability of those particles. Furthermore, these fine powders are scattered as dust and it is impossible to completely avoid contamination of the working environment. In the process in which a powdery N-alkyl-N'-phenyl-p-phenylenediamine is dispersed in water, dust scattering is caused at the dispersing step, also contaminating the environment. Moreover, the process of recovering the organic solvent becomes necessary, which is not advantageous from the industrial viewpoint.

SUMMARY OF THE INVENTION

It is therefore a primary object of the present invention to provide a process for the preparation of N-alkyl-N'-phenyl-p-phenylenediamine particles which do not generate powder during transportation or in a hopper and can be easily automatically metered.

In accordance with the present invention, there is provided a process for the surface treatment of N-alkyl-N'-phenyl-p-phenylenediamine particles, which comprises charging granulated N-alkyl-N'-phenyl-p-phenylenediamine particles in a rotatable vessel and rotating the vessel at a temperature lower than the melting point of the N-alkyl-N'-phenyl-p-phenylenediamine, to cause the N-alkyl-N'-phenyl-p-phenylenediamine particles to freely flow.

DESCRIPTION OF THE PREFERRED EMBODIMENTS

N-alkyl-N'-phenyl-p-phenylenediamines treated in the process of the present invention are solid at room temperature, and those having a melting point not higher than 80° C. can be advantageously treated according to the present invention. Most N-alkyl-N'-phenyl-p-phenylenediamines having a melting point not higher than 80° C. have 3 to 8 carbon atoms in the alkyl group inclusive of the branched chain. For example, there can be mentioned N-sec.-heptyl-N'-phenyl-p-phenylenediamines such as N-(1,4-dimethylpentyl)-N'-phenyl-p-phenylenediamine and N-(1-methylhexyl)-N'-phenyl-p-phenylenediamine, N-sec.-hexyl-N'-phenyl-p-phenylenediamines such as N-(1,3-dimethylbutyl)-N'-phenyl-p-phenylenediamine and N-(1-methylpentyl)-N'-phenyl-p-phenylenediamine, and N-isopropyl-N'-phenyl-p-phenylenediamine. Of course, the alkyl group may be a primary alkyl group. Furthermore, these diamines may be used either alone or as a mixture of two or more thereof, but a mixture of N-alkyl-N'-phenyl-p-phenylenediamines having a relatively low melting point is not preferred. The process of the present invention is especially suitable for the surface treatment of particles of N-(1,4-dimethylpentyl)-N'-phenyl-p-phenylenediamine, N-(1,3-dimethylbutyl)-N'-phenyl-p-phenylenediamine and N-isopropyl-N'-phenyl-p-phenylenediamine, and is most effective for the surface treatment of particles of N-(1,3-dimethylbutyl)-N'-phenyl-p-phenylenediamine. Note, N-(1,4-dimethylpentyl)-N'-phenyl-p-phenylenediamine has a melting point of 32° to 34° C., N-(1,3-dimethylbutyl)-N'-phenyl-p-phenylenediamine has a melting point of 44° to 49° C., and N-isopropyl-N'-phenyl-p-phenylenediamine has a melting point of 72° to 80° C. Other phenylenediamines mentioned above have melting points similar to those of the phenylenediamines having a similar structure.

The method for the granulation of N-alkyl-N'-phenyl-p-phenylenediamines is not particularly critical. For example, there can be mentioned: (1) a method in which a melt of an N-alkyl-N'-phenyl-p-phenylenediamine is dispersed in an aqueous solution containing a surface active agent (see Japanese Examined Patent Publication No. 58-10422 and Japanese Unexamined Patent Publication No. 58-74734); (2) a method in which a melt of an N-alkyl-N'-phenyl-p-phenylenediamine is dropped to be dispersed in an aqueous solution containing a hydrophilic polymeric compound (see Japanese Examined Patent Publication No. 48-3210); (3) a method in which a melt of an N-alkyl-N'-phenyl-p-phenylenediamine is dropped on a steel belt (see Japanese Unexamined Patent Publication No. 58-39647); and, (4) a method in which a powdery N-alkyl-N'-phenyl-p-phenylenediamine is dispersed in water containing 0 to 30% by weight of an organic solvent and the dispersion is then heated at a temperature lower than the boiling point of water to effect granulation (see Japanese Unexamined Patent Publication No. 54-62245). In the methods (1) through (3), since the melt is rapidly cooled, an aggregate of fine crystals is formed and this aggregate is readily broken by a slight impact force or the like, and thus fine powders are formed in large amounts and adhere to the surface of particles. This phenomenon of the adhesion of fine powders is prominent in method (3) wherein granulation is effected in the absence of water, that is, a melt of an N-alkyl-N'-phenyl-p-phenylenediamine is dropped to be cooled on a steel belt. Thus, the process of the present invention is most suitable for the surface treatment of N-alkyl-N'-phenyl-p-phenylenediamine particles granulated according to the method (3). It is preferred that the particle size of the N-alkyl-N'-phenyl-p-phenylenediamine used in the present invention be 0.1 to 15 mm, more preferably 1 to 10 mm.

The rotatable vessel used in the present invention is not particularly critical, but it is preferred that the structure of the vessel be such that when the N-alkyl-N'-phenyl-p-phenylenediamine particles are charged in the vessel, impact shock from falling or the like is not given to the particles but the particles are allowed to freely flow. More specifically, it is preferable to adopt a lateral cylindrical vessel rotating around the central axis of the cylinder or a cylindrical vessel arranged at a slight angle of inclination to the horizontal plane. The vessel may be provided with a heating mechanism or cooling mechanism for adjusting the inner temperature of the vessel. The size of the vessel depends on the amount of particles to be surface-treated and the rotation speed of the vessel. However, a vessel having a space allowing the particles to freely flow with the rotation of the vessel should be appropriately selected.

In carrying out the process of the present invention, N-alkyl-N'-phenyl-p-phenylenediamine particles are charged in a rotatable vessel in such an amount that the particles occupy 5 to 80%, preferably 20 to 70%, of the volume of the vessel. The vessel is then rotated around the center of the rotation axis of the vessel to cause the particles to freely flow. When the surface treatment is carried out according to the present invention, it is indispensable that the temperature of the rotatable vessel should be lower than the melting temperature of the N-alkyl-N'-phenyl-p-phenyleneediamine. It is preferred that the vessel be rotated at a temperature at least 4° C. lower than the melting temperature of the N-alkyl-N'-phenyl-p-phenylenediamine. For example, in the case of N-(1,3-dimethyl-butyl)-N'-phenyl-p-phenylenediamine, the rotation should be carried out at room temperature to 40° C., preferably 35° to 40° C. Since the temperature of the particles naturally rises during the free flowing thereof, the particle temperature is appropriately adjusted so that it will not rise above the melting temperature, if necessary. The time for rotation of the vessel is appropriately determined depending upon the surface conditions of N-alkyl-N'-phenyl-p-phenylenediamine particles or the breaking strength of the particles. Ordinarily, the rotation time may be decided by observing the surface conditions of the particles. In the present invention, better results are obtained when the rotation is effected at a low speed and continued for a long time, though the preferred rotation time will differ in accordance with the space ratio in the vessel.

The surface treatment may be conducted according to a batchwise method in which the particles are charged in a sealed rotary vessel and the vessel is rotated, or a continuous method in which particles are supplied from an inlet formed on the upper part of a long cylindrical vessel arranged at a slight angle of inclination to the horizontal plane and the treated particles are discharged from an outlet arranged in the lower portion of the vessel.

In the N-alkyl-N'-phenyl-p-phenylenediamine particles which have been thus caused to freely flow, fine powders are not found to adhere to the surfaces of the particles. It can be clearly seen that the fine powders have been integrated with the particles to form smooth surfaces. In some cases, the surfaces of the particles have a gloss resembling a gloss formed by melting, and the adhesion of fine powders to the interior of the vessel or the vessel wall is not observed at all.

According to the surface treatment of the present invention, solid particles of an N-alkyl-N'-phenyl-pphenylenediamine having no adhering powders, a good flowability, and smooth particle surfaces can be obtained. These particles are rarely broken during transportation or in a hopper, and thus are advantageous over conventional brittle particles formed only by granulation.

Therefore, in the particles prepared according to the process of the present invention, agglomeration or compaction with the fine powders does not occur and automatic metering can be performed very easily. Also, clogging of the discharge opening of a hopper can be prevented. Furthermore, according to the present invention, N-alkyl-N'-phenyl-p-phenylene particles are only rotated in a rotatable vessel to be made to freely flow therein. Namely, a complicated sieving operation becomes unnecessary and contamination of the environment by dust can be prevented.

The process of the present invention will now be described in detail with reference to the following examples that by no means limit the scope of the invention.

EXAMPLES

Two kinds of N-(1,3-dimethylbutyl)-N'-phenyl-p-phenylenediamine particles having a particle diameter of 3 to 4 mm or 5 to 6 mm were prepared by a method wherein a melt of N-(1,3-dimethylbutyl)-N'-phenyl-p-phenylenediamine was dropped on a steel belt. The two kinds of the particles were separately charged in a lateral cylindrical vessel having a diameter of 500 mm and a length of 600 mm, so that the volume ratio was as shown in Table 1. The vessel was then closed and rotated at a rotation speed of 15 rpm or 60 rpm adjusted by a motor provided with a reduction gear, and the particles were allowed to freely flow in the rotated vessel for a predetermined time. The temperature of the rotated vessel was initially room temperature and finally elevated to 36° C. at highest. The yield after the surface treatment was 100% at the rotation speed of 15 rpm and 99% or more at the rotation speed of 60 rpm.

The flowability, surface appearance, and compression strength of the surface-treated particles are determined according to the following procedures, and the obtained results are shown in Table 1. Data of untreated N-(1,3-dimethylbutyl)-N'-phenyl-p-phenylenediamine are shown for comparison.

Flowability:
Flowability evaluated by the naked eye.
Surface appearance:
Surface appearance examined by the naked eye.
Adhesion of fine powders:
The state of adhesion of fine powders to particles was observed.
Smoothness:
The smoothness was evaluated according to the 5-scale method, in which the smoothness of the untreated particles was judged as class 1 and the smoothness of the particles treated at 15 rpm at a volume ratio of 30% for 120 minutes was judged as class 5.
Compression strength:
The breaking strength of all the particles was measured under the same conditions, and the breaking strength was evaluated according to the 5-scale method in which the lowest breaking strength was judged as class 1 and the highest breaking strength was judged as class 5.

claim 1, wherein the rotatable vessel is a lateral cylindrical vessel which rotates around the central axis of the cylinder.

3. A process for the surface treatment of N-alkyl-N'-phenyl-p-phenylenediamine particles according to claim 1 or 2, wherein the rotatable vessel is arranged at a slight angle of inclination to the horizontal plane.

4. A process for the surface treatment of N-alkyl-N'-phenyl-p-phenylenediamine particles according to claim 1, wherein the alkyl group of the N-alkyl-N'-p-phenylenediamine has 3 to 8 carbon atoms.

5. A process for the surface treatment of N-alkyl-N'-phenyl-p-phenylenediamine particles according to claim 4, wherein the N-alkyl-N'-phenyl-p-phenylenediamine is an N-sec.-hexyl-N'-phenyl-p-phenylenediamine or N-sec.-heptyl-N'-phenyl-p-phenylenediamine.

6. A process for the surface treatment of N-alkyl-N'-phenyl-p-phenylenediamine particles according to claim 4, wherein the N-alkyl-N'-phenyl-p-phenylenediamine is an N-isopropyl-N'-phenyl-p-phenylenediamine or N-(1,3-dimethylbutyl)-N'-phenyl-p-phenylenediamine.

7. A process for the surface treatment of N-alkyl-N'phenyl-p-phenylenediamine particles wherein said particles do not generate powder during transportation or undergo agglomeration, said process consisting essentially of charging granulated N-alkyl-N'phenyl-p-phenylenediamine particles in a rotatable vessel, and rotating the vessel at a temperature lower than the melting point of the N-alkyl-N'phenyl-p-phenylenediamine to cause the N-alkyl-N'phenyl-p-phenylenediamine particles to freely flow.

8. A process for the surface treatment of N-alkyl-N'phenyl-p-phenylenediamine particles wherein said particles do not generate powder during transportation

TABLE 1

| | Example No. | | | | | | | | | | | | Comparision |
|---|---|---|---|---|---|---|---|---|---|---|---|---|---|
| | 1 | | | | | | 2 | | | 3 | | | |
| Volume ratio (%) | 30 | | | | | | 50 | | | 70 | | | — |
| Particle diameter (mm) | 3–4 | | | | | 5–6 | 3–4 | | 5–6 | 3–4 | | 5–6 | 3–4 |
| Rotation speed (r.p.m.) | 15 | | | | 60 | | 15 | 15 | 15 | 15 | | 60 | — |
| Rotation time (minutes) | 30 | 60 | 90 | 120 | 30 | 120 | 120 | 120 | 120 | 120 | 30 | 120 | — |
| Flowability | Good | Good | Good | Good | Good | Good | Good | Good | Good | Good | Good | Good | Bad |
| Surface appearance | Good | Good | Good | Good | Good | Relatively bad | Good | Good | Good | Good | Relatively bad | Relatively bad | Bad |
| Adhesion of fine powders | Not observed | Not observed | Not observed | Not observed | Not observed | Not observed | Not observed | Not observed | Not observed | Not observed | Not observed | Not observed | Observed |
| Smoothness | 2 | 3 | 4 | 5 | 3 | 3 | 5 | 5 | 5 | 5 | 5 | 3 | 1 |
| Compression strength | 2 | 3 | 3 | 4 | 3 | 2 | 5 | 2 | 5 | 3 | 3 | 4 | 1 |

I claim:

1. A process for the surface treatment of N-alkyl-N'-phenyl-p-phenylenediamine particles, which comprises charging granulated N-alkyl-N'-phenyl-p-phenylenediamine particles in a rotatable vessel, and rotating the vessel at a temperature lower than the melting point of the N-alkyl-N'-phenyl-p-phenylenediamine to cause the N-alkyl-N'-phenyl-p-phenylenediamine particles to freely flow.

2. A process for the surface treatment of N-alkyl-N'-phenyl-p-phenylenediamine particles according to or undergo agglomeration, said process consisting essentially of charging in a rotatable vessel granulated N-alkyl-N'phenyl-p-phenylenediamine particles in a rotatable vessel.

9. The process of claim 7 wherein the particle size of said N-alkyl-N'phenyl-p-phenylenediamine is from 0.1 to 15 mm.

10. The process of claim 7 wherein the particle size of said N-alkyl-N'phenyl-p-phenylenediamine is from 1 to 10 mm.

* * * * *